United States Patent
Merkel et al.

(10) Patent No.: US 10,207,972 B2
(45) Date of Patent: *Feb. 19, 2019

(54) AZEOTROPIC COMPOSITIONS OF 1,3,3,3-TETRACHLOROPROP-1-ENE AND HYDROGEN FLUORIDE

(71) Applicant: Honeywell International Inc., Morris Plains, NJ (US)

(72) Inventors: Daniel C. Merkel, Orchard Park, NY (US); Konstantin A. Pokrovski, Spencerport, NY (US); Hsueh Sung Tung, Getzville, NY (US); Haiyou Wang, Amherst, NY (US); Ryan Hulse, Getzville, NY (US)

(73) Assignee: Honeywell international Inc., Morris Plains, NJ (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/955,459

(22) Filed: Dec. 1, 2015

(65) Prior Publication Data

US 2016/0083317 A1    Mar. 24, 2016

Related U.S. Application Data

(63) Continuation of application No. 13/798,385, filed on Mar. 13, 2013, now Pat. No. 9,222,177.

(51) Int. Cl.
| | | |
|---|---|---|
| *C09K 5/04* | (2006.01) | |
| *C23G 5/028* | (2006.01) | |
| *C11D 7/08* | (2006.01) | |
| *C11D 7/50* | (2006.01) | |
| *C07C 21/18* | (2006.01) | |
| *C07C 21/04* | (2006.01) | |
| *C07C 19/08* | (2006.01) | |

(52) U.S. Cl.
CPC .............. *C07C 21/18* (2013.01); *C07C 19/08* (2013.01); *C07C 21/04* (2013.01); *C11D 7/08* (2013.01); *C11D 7/5036* (2013.01); *C23G 5/02806* (2013.01); *C09K 5/044* (2013.01)

(58) Field of Classification Search
CPC ......... C07C 19/01; C07C 17/38; C07C 21/04; C07C 21/18; C07C 19/08; C09K 3/00; C09K 5/044; C01B 7/19; F25J 3/08; C23G 5/02806; C11D 7/08; C11D 7/5036
USPC ........................................................ 252/364
See application file for complete search history.

(56) References Cited

U.S. PATENT DOCUMENTS

| | | |
|---|---|---|
| 5,616,819 A | 4/1997 | Boyce et al. |
| 5,811,603 A | 9/1998 | Elsheikh |
| 5,877,359 A | 3/1999 | Elsheikh |
| 6,013,846 A | 1/2000 | Wismer et al. |
| 6,166,274 A | 12/2000 | Chen et al. |
| 7,183,448 B2 | 2/2007 | Nakada et al. |

(Continued)

OTHER PUBLICATIONS

Extended European Search Report dated Sep. 29, 2016 in Appln. No. 14774035.1.

(Continued)

*Primary Examiner* — Daniel S Metzmaier

(57) ABSTRACT

Provided are azeotropic or azeotrope-like mixtures of 1,3,3,3-tetrachloroprop-1-ene (HCO-1230zd) and hydrogen fluoride. Such compositions are useful as a feed stock in the production of HFC245fa and HCFO1233zd.

11 Claims, 1 Drawing Sheet

(56) References Cited

U.S. PATENT DOCUMENTS

| | | | |
|---|---|---|---|
| 8,008,243 B2 * | 8/2011 | Tung | C01B 7/191 |
| | | | 510/407 |
| 8,207,383 B2 | 6/2012 | Deur-Bert et al. | |
| 8,309,774 B2 | 11/2012 | Pigamo et al. | |
| 8,367,878 B2 | 2/2013 | Merkel et al. | |
| 9,222,177 B2 * | 12/2015 | Merkel | C07C 21/04 |
| 2009/0227822 A1 | 9/2009 | Pham et al. | |
| 2011/0155942 A1 | 6/2011 | Pigamo et al. | |
| 2011/0201853 A1 | 8/2011 | Tung et al. | |
| 2011/0287996 A1 | 11/2011 | Tung et al. | |
| 2012/0059199 A1 | 3/2012 | Pokrovski et al. | |
| 2012/0215039 A1 | 8/2012 | Hulse et al. | |
| 2013/0221272 A1 | 8/2013 | Merkel et al. | |
| 2014/0221704 A1 | 8/2014 | Tung et al. | |

OTHER PUBLICATIONS

PCT ISR & Written Opinion issued in PCT/US2014/020645 dated Jun. 26, 2014.

* cited by examiner

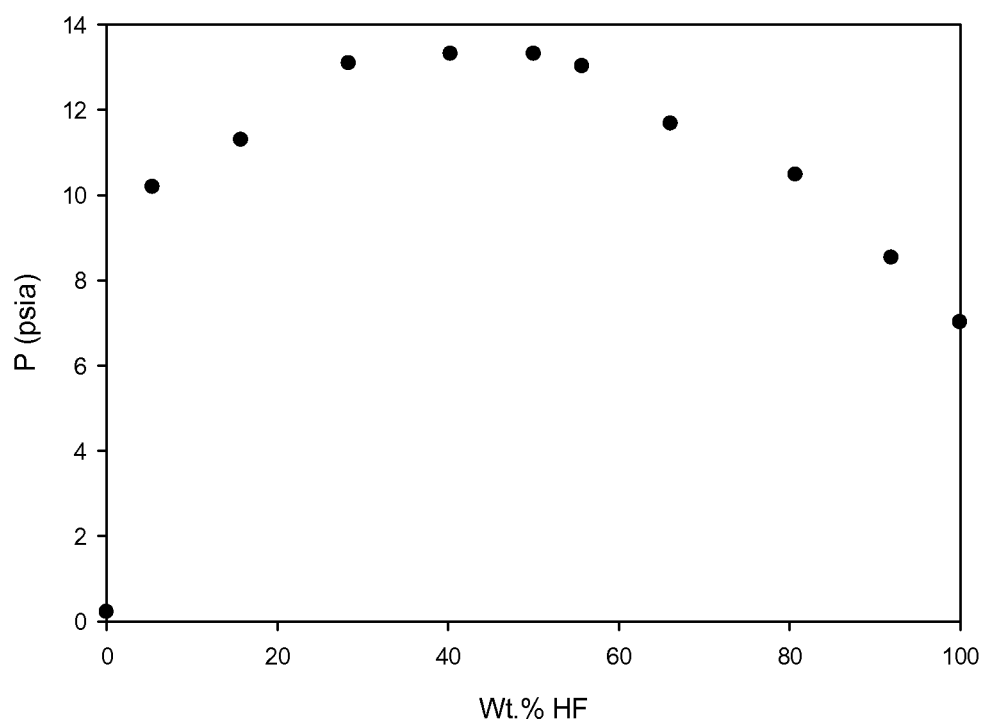

AZEOTROPIC COMPOSITIONS OF 1,3,3,3-TETRACHLOROPROP-1-ENE AND HYDROGEN FLUORIDE

CROSS-REFERENCE TO RELATED APPLICATION

This application is a continuation of application Ser. No. 13/798,385, filed Mar. 13, 2013, now U.S. Pat. No. 9,222,177 B2 the disclosure of which is hereby incorporated herein by reference.

FIELD OF THE INVENTION

The present invention pertains to azeotropic or azeotrope-like compositions of 1,3,3,3-tetrachloroprop-1-ene (HCO-1230zd) and hydrogen fluoride (HF).

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. The use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

1,3,3,3-tetrachloroprop-1-ene (HCO-1230zd) is the reactant in the production of both 245fa and 1233zd which are well known in the art as described in U.S. Pat. Nos. 5,763,706 and 6,844,475, respectively. In the case of 1233zd, see U.S. Patent Pub. No. 2011-0201853. These documents are hereby incorporated herein by reference.

It has now surprisingly been found that an important feed stock in the production of both 245fa and 1233zd, is an azeotrope or azeotrope-like mixture of 1,3,3,3-tetra-chloroprop-1-ene (HCO-1230zd) and hydrogen fluoride (HF). This mixture, once formed, may thereafter be separated into its component parts by extraction or distillation techniques. HCO-1230zd has a boiling point of about 145° C. and HF has a boiling point of about 20° C. at standard atmospheric pressure. The azeotropic or azeotrope-like compositions find use not only as reactor feeds in the production of 245fa and 1233zd, but they are additionally useful as solvent compositions for removing surface oxidation from metals.

SUMMARY OF THE INVENTION

The invention provides a heterogeneous azeotropic composition consisting essentially of 1,3,3,3-tetrachloroprop-1-ene (HCO-1230zd) and hydrogen fluoride (HF).

The invention further provides an azeotropic or azeotrope-like composition which consists essentially of from about 0.2 to about 99 weight percent hydrogen fluoride and from about 99.8 to about 1 weight percent 1,3,3,3-tetrachloroprop-1-ene (HCO-1230zd), which composition has a boiling point of about 0° C., at pressure of about 13.3 psia.

The invention also provides a method of forming a heterogeneous azeotropic or azeotrope-like composition which consists essentially of from about 1 to about 99 weight percent hydrogen fluoride and from about 99 to about 1 weight percent 1,3,3,3-tetra-chloroprop-1-ene (HCCO-1230zd), which composition has a boiling point of about from 0° C., at pressure of about from 13.3 psia.

The invention also provides a method of forming a heterogeneous azeotropic or azeotrope-like composition which consists essentially of blending from about 0.2 to about 97 weight percent hydrogen fluoride and from about 99.8 to about 3 weight percent 1,3,3,3-tetrachloroprop-1-ene (HCO-1230zd), which composition has a boiling point of about from 0° C., at pressure of about from 13.3 psia.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWING

FIG. 1 shows a plot of the vapor pressures of the mixtures formed in Example 1 as measured at 0° C.

DETAILED DESCRIPTION OF THE PREFERRED EMBODIMENT

It has surprisingly been discovered that when 1,3,3,3-tetrachloroprop-1-ene (HCO-1230zd) and HF were fed to a reactor, 1230zd forms azeotropic or azeotrope-like mixtures with HF. The unreacted 1230zd/HF mixture was found in the product stream.

The thermodynamic state of a fluid is defined by its pressure, temperature, liquid composition and vapor composition. For a true azeotropic composition, the liquid composition and vapor phase are essentially equal at a given temperature and pressure. In practical terms this means that the components cannot be separated during a phase change.

For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions, which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures.

Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and 1230zd to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with 1230zd.

In a preferred embodiment, the inventive composition contains from about 99 to about 1 weight percent HF, preferably from about 90 weight percent to about 10 weight percent and most preferably from about 70 weight percent to about 15 weight percent. In another preferred embodiment, the inventive composition contains from about 1 to about 99 weight percent 1230zd preferably from about 10 weight percent to about 90 weight percent and most preferably from about 30 weight percent to about 85 weight percent.

Preferred compositions of the present invention have a boiling point of about 0° C. at a pressure of about 13.3 psia. An azeotropic or azeotrope-like composition having about 39±2 weight percent HF and about 61±2 weight percent 1230zd has been found to boil at about 0° C., at 13.3 psia.

The following non-limiting examples serve to illustrate the invention.

Example 1

14.4 g of 1,3,3,3-tetrachloroprop-1-ene (HCO-1230zd) were combined with 14.4 g of HF to form a heterogeneous azeotrope mixture. This experiment was done at 0° C., and at 13.3 psia (by visual observation).

Example 2

Binary compositions containing solely 1,3,3,3-tetrachloroprop-1-ene (HCO-1230zd) and HF are blended to form heterogeneous azeotrope mixtures at different compositions. The vapor pressures of the mixtures are measured at 0° C. and the following results are noticed.

Table 1 shows the vapor pressure measurement of 1230zd and HF as a function of composition of weight percent HF at constant temperatures of about 0° C. The data from Table 1 are shown in graphic form in FIG. 1.

TABLE 1

| P-T-X of 1230zd/HF at T = 0° C. | |
| --- | --- |
| Wt. % HF | P (psia) |
| 0.0 | 0.2 |
| 5.4 | 10.2 |
| 15.8 | 11.3 |
| 28.4 | 13.1 |
| 40.3 | 13.3 |
| 50.1 | 13.3 |
| 55.7 | 13.0 |
| 66.1 | 11.7 |
| 80.7 | 10.5 |
| 92.0 | 8.5 |
| 100.0 | 7.0 |

These data also show that the mixture is an azeotrope since the vapor pressures of mixtures of 1230zd and HF are higher, at all indicated blend proportions, than 1230zd and HF alone, i.e., as indicated in the first and last rows when HF is 0.0 wt % and 1230zd is at 100.0 wt % as well as when 1230zd is at 0.0 wt % and HF is at 100.0 wt. %.

Example 3

The azeotropic composition of the 1230zd/HF mixture is also verified by Vapor-Liquid-Liquid Equilibrium (VLLE) experiment. 14.6 g of 1,1,3,3-tetrachloroprop-1-ene (HCO-1230zd) were combined with 13.2 g of HF to form a heterogeneous mixture (visual observation) at 0° C. The vapor compositions of the mixture were sampled at temperature of 0° C. and at pressure of 13.3 psia. The result shows that the azeotropic composition is about 39±2 wt % HF at 0° C.

This mixture is observed to be a heterogeneous azeotrope at a temperature of 0° C. and pressure of 13.3 psia.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A composition consisting of 1,3,3,3-tetrachloroprop-1-ene (HCO-1230zd) and hydrogen fluoride, wherein the amount of hydrogen fluoride in the composition ranges from about 5.4 to about 92 weight percent and wherein the composition is a heterogeneous binary azeotrope or azeotrope-like composition.

2. The composition of claim 1, wherein the amount of hydrogen fluoride in the composition is 5.4 weight percent.

3. The composition of claim 1, wherein the amount of hydrogen fluoride in the composition is 15.8 weight percent.

4. The composition of claim 1, wherein the amount of hydrogen fluoride in the composition is 28.4 weight percent.

5. The composition of claim 1, wherein the amount of hydrogen fluoride in the composition is 40.3 weight percent.

6. The composition of claim 1, wherein the amount of hydrogen fluoride in the composition is 50.1 weight percent.

7. The composition of claim 1, wherein the amount of hydrogen fluoride in the composition is 55.7 weight percent.

8. The composition of claim 1, wherein the amount of hydrogen fluoride in the composition is 66.1 weight percent.

9. The composition of claim 1, wherein the amount of hydrogen fluoride in the composition is 80.7 weight percent.

10. The composition of claim 1, wherein the amount of hydrogen fluoride in the composition is 92.0 weight percent.

11. A composition consisting of 14.4 g of 1,3,3,3-tetrachloroprop-1-ene (HCO-1230zd) and 14.4 g of HF, wherein the composition is a heterogeneous binary azeotrope or azeotrope-like composition which has a boiling point of about 0° C. at a pressure of about 13.3 psia.

* * * * *